(12) United States Patent
Kovarik et al.

(10) Patent No.: US 8,585,114 B2
(45) Date of Patent: Nov. 19, 2013

(54) SELECTIVELY BENDABLE REMOTE GRIPPING TOOL

(71) Applicants: Carter J. Kovarik, Englewood, CO (US); Joseph E. Kovarik, Englewood, CO (US)

(72) Inventors: Carter J. Kovarik, Englewood, CO (US); Joseph E. Kovarik, Englewood, CO (US)

( * ) Notice: Subject to any disclaimer, the term of this patent is extended or adjusted under 35 U.S.C. 154(b) by 0 days.

(21) Appl. No.: 13/771,813

(22) Filed: Feb. 20, 2013

(65) Prior Publication Data

US 2013/0214547 A1 Aug. 22, 2013

Related U.S. Application Data

(60) Provisional application No. 61/601,789, filed on Feb. 22, 2012.

(51) Int. Cl.
*B25J 1/02* (2006.01)

(52) U.S. Cl.
USPC ............................. 294/209; 294/210; 294/111

(58) Field of Classification Search
USPC ......... 294/111, 115, 209, 210, 190; 81/177.6; 606/205
See application file for complete search history.

(56) References Cited

U.S. PATENT DOCUMENTS

| 388,776 A | 8/1888 | Hall | |
|---|---|---|---|
| 826,160 A | 7/1906 | Hall | |
| 944,214 A | 12/1909 | Rydquist | |
| 1,051,374 A | 1/1913 | Agin | |
| 1,519,938 A * | 12/1924 | Smith | 81/383 |
| 2,613,100 A | 10/1952 | Casey | |
| 2,616,741 A | 11/1952 | Ziese | |
| 2,947,564 A * | 8/1960 | Winther | 294/100 |
| 3,219,376 A | 11/1965 | Peters | |
| 3,266,059 A * | 8/1966 | Stelle | 623/62 |
| 3,346,293 A | 10/1967 | Wilcox | |
| 3,527,492 A | 9/1970 | Hollis | |
| 3,576,343 A | 4/1971 | Juhlin et al. | |
| 3,761,121 A | 9/1973 | Reid | |
| 3,934,915 A | 1/1976 | Humpa | |
| 4,033,618 A * | 7/1977 | Lamb | 294/104 |
| 4,039,216 A | 8/1977 | Soos | |
| 4,253,697 A * | 3/1981 | Acosta | 294/115 |
| 4,374,600 A | 2/1983 | van Zelm | |
| 4,393,728 A * | 7/1983 | Larson et al. | 74/469 |
| 4,398,759 A | 8/1983 | Manola | |
| 4,483,562 A * | 11/1984 | Schoolman | 294/104 |

(Continued)

FOREIGN PATENT DOCUMENTS

FR 1080718 12/1954

OTHER PUBLICATIONS

"Robot Claw Grabber" by Toysmith, Feb. 27, 2005, [retrieved on Aug. 16, 2013], 3 pages. Retrieved from: http://web.archive.org/web/20050227054600/http://www.toys2wish4.com/robclawgrab.html.
U.S. Appl. No. 29/462,798, filed Aug. 8, 2013, Kovarik et al.

*Primary Examiner* — Dean Kramer
(74) *Attorney, Agent, or Firm* — Sheridan Ross P.C.

(57) ABSTRACT

A hand-held remote access device, such as a gripping tool, includes a jaw portion having a pair of jaws movable relative to each other between fully clamped and fully opened positions thereof, a handle portion spaced apart from the jaw portion by a bendable central portion that has a hollow, corrugated member having alternating ridges and grooves that is bendable so as to attain a predetermined shape.

25 Claims, 4 Drawing Sheets

(56) References Cited

U.S. PATENT DOCUMENTS

| | | |
|---|---|---|
| 4,613,179 A | 9/1986 | van Zelm |
| 4,647,094 A | 3/1987 | Bergkvist et al. |
| 4,669,769 A | 6/1987 | Polder, Jr. |
| 4,709,839 A | 12/1987 | Tucker |
| 4,758,035 A | 7/1988 | Shimasaki |
| 4,863,204 A | 9/1989 | Peters |
| 4,962,957 A | 10/1990 | Traber |
| 5,154,465 A | 10/1992 | Pakosh |
| 5,380,054 A | 1/1995 | Galvis |
| 5,577,785 A | 11/1996 | Traber et al. |
| 5,590,923 A | 1/1997 | Berger et al. |
| 5,647,622 A * | 7/1997 | Schectman .................. 294/111 |
| 5,766,196 A * | 6/1998 | Griffiths ....................... 606/170 |
| 5,823,592 A * | 10/1998 | Kalidindi ........................ 294/24 |
| 5,857,723 A | 1/1999 | Mathieu et al. |
| 5,895,082 A | 4/1999 | Kaluzny |
| 6,257,634 B1 | 7/2001 | Wei |
| 6,457,761 B1 | 10/2002 | Benoit |
| 6,508,496 B1 | 1/2003 | Huang |
| 6,513,844 B1 | 2/2003 | Hsu |
| 6,520,556 B1 | 2/2003 | Hsu |
| 6,571,479 B1 | 6/2003 | Wu |
| 6,669,254 B2 | 12/2003 | Thom et al. |
| 6,739,637 B2 | 5/2004 | Hsu |
| 6,848,731 B2 | 2/2005 | Khubani et al. |
| 6,874,833 B2 | 4/2005 | Keith et al. |
| 7,004,520 B2 | 2/2006 | Khubani et al. |
| 7,344,171 B1 | 3/2008 | McMullan |
| D591,122 S | 4/2009 | Buzby et al. |
| 7,665,782 B2 | 2/2010 | Buzby et al. |
| 7,854,738 B2 * | 12/2010 | Lee et al. ...................... 606/130 |
| D632,069 S | 2/2011 | Thiessens |
| 7,934,756 B2 * | 5/2011 | Kroeze ......................... 294/210 |
| 7,980,609 B2 | 7/2011 | Khubani |
| 8,061,751 B2 | 11/2011 | Hatcher |
| 8,091,936 B1 | 1/2012 | Graziano |
| 2003/0236549 A1 * | 12/2003 | Bonadio et al. ............... 606/205 |
| 2005/0057055 A1 | 3/2005 | Deal |
| 2010/0021279 A1 | 1/2010 | Buzby et al. |
| 2012/0060878 A1 | 3/2012 | Thiessens |

\* cited by examiner

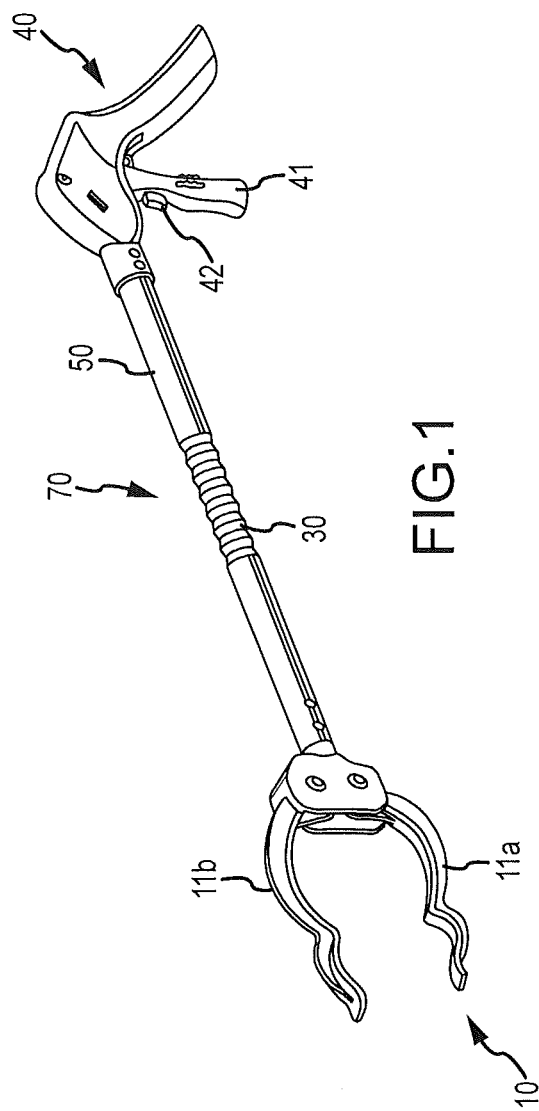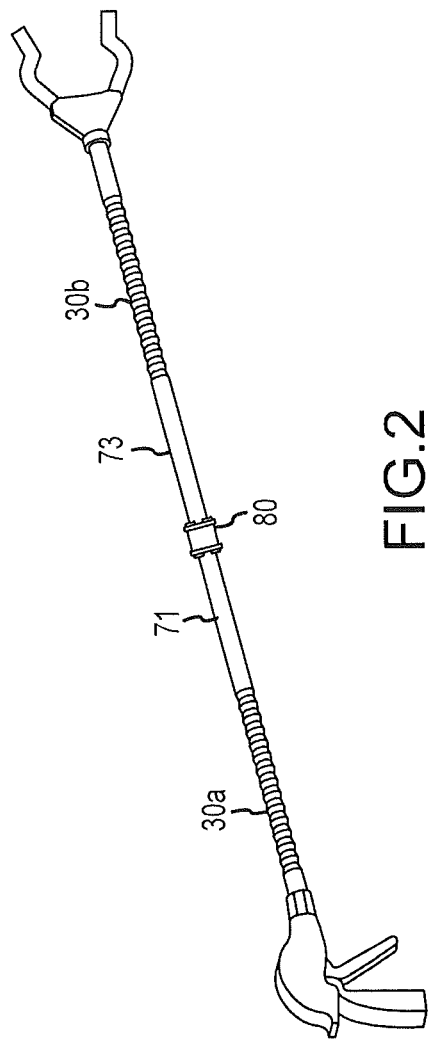

SELECTIVELY BENDABLE REMOTE GRIPPING TOOL

RELATED APPLICATIONS

This application claims priority from U.S. Provisional Patent Application Ser. No. 61/601,789, filed on Feb. 22, 2012. The entire disclosure of the prior application is considered to be part of the disclosure of the accompanying application and is hereby incorporated by reference.

FIELD OF THE INVENTION

The present invention is directed to a hand-held device used for gripping objects or in achieving other remote functions, such device having at least one corrugated member that is bendable to position a remote end of such device into a desired orientation.

BACKGROUND OF THE INVENTION

Hand-held gripping devices for picking up and gripping objects have been known for years and typically employ a jaw portion and a handle portion spaced apart by a central portion. Such "grippers" typically have fixed-length central portions, although some have two part construction that permits a pivot point around the central portion of the device so that it can be stored more easily, and still others have telescoping portions to facilitate adjustable-length central portions.

There is a long felt but unsolved need for a remote access tool, such as a gripping device, that facilitates a user's ability to reach around corners or other angles that are not accessible via the use of traditional remote access tools that have non-bendable, straight central portions.

SUMMARY OF THE DISCLOSURE

The specification describes a hand-held gripping device, comprising a jaw portion having a pair of jaws movable relative to each other between fully clamped and fully opened positions thereof, and a handle portion spaced apart from the jaw portion by a central portion, which in some embodiments may be adjustable in length via telescoping portions slidingly moved to attain a desired length. The handle portion comprises a manually-actuatable trigger (although in other embodiments the activation of the trigger is via an electronic button) operatively connected to the jaw portion by a selectively extendible pull member at least substantially disposed within the central portion. Actuation of the trigger is operative to move the pull member to thereby selectively position the pair of jaws between the fully clamped and fully opened position thereof. The selectively extendible central portion may comprise a first tubular member and, if the device is adjustable with respect to its length, may employ rotatable locking members to reversibly lock the respective portions of the central column into a fixed position. In certain embodiments, the central portion comprises a hollow, corrugated member having alternating ridges and grooves, such member being bendable so as to attain a predetermined shape. Suitable material for use in the central column will be known by those of skill in the art, but, for example, hoses used for connecting gas appliances, such as coated, stainless steel gas connector hose is suitable for many embodiments as it reversibly bends via simple manual adjustment (or in certain embodiments, via a separate trigger element) into various desired directions and retains its bent position until further altered by the user. Alternative materials can be selected for various desired attributes, such as weight, cost, color, temperature characteristics, rigidity, corrosion resistance, electrical conductivity, water permeability, glow in the dark characteristics, etc. Thus, suitable connector material for use as the entire, or alternatively only a portion of the central portion of the gripping device, may comprise a hollow, corrugated member having alternating ridges and grooves, such member being bendable so as to attain a predetermined shape, and may be made of a variety of materials, including plastic, metal, and composites. The bendable portion of the central portion can be selectively or in a predetermined manner configured into a shape so as to facilitate easier access to a desired area, object, etc. The reversible nature of the bendable nature of the tool provides a user with the ability to adjust the angle of the distal portion of the tool to accommodate the myriad of difficult angles encountered by a user. Traditional remote access tools, which have straight and non-bending (as opposed to merely pivoting or telescoping) portions, are not able to achieve the desired remote access as provided by the present invention.

Extendable tools are typically used to interact with overhead objects that may be close or remote. For example, a fruit picker may be able to reach fruit; a janitor to replace light bulbs, and elderly person to grasp objects near their chair, tree pruners to reach certain limbs in particular orientations, etc. All of these various functions are made vastly easier by the provision of applicable forms of embodiments of the present invention as described in more detail (with respect to illustrative embodiments that one of skill in the art will appreciate transcend the particular field employed for illustrative purposes.)

In certain embodiments, at least one cord is employed that operatively connects the handle portion to the jaw portion, with such at least one cord extending through said central portion and through the hollow, corrugated member having alternating ridges and grooves. In certain embodiments, only the distal portion of the device has a segment of the hollow, corrugated member so as to limit the weight characteristics of such material as compared to the overall device. In certain embodiments, the hand-held gripping device has at least $\tfrac{2}{3}^{rd}$ of said central portion comprises said corrugated member. It has been found, however, that providing ten inches of such material is sufficient for many circumstances where a user desires to perform the desired bend to facilitate reaching an object to engage with the jaws of the device. As one will appreciate, however, any length of the hollow, corrugated member having alternating ridges and grooves can be used depending upon the circumstances. Thus, while in some embodiments, substantially the entire central portion comprises such material, in other embodiments, one or more sections of the central portion comprise such a hollow, corrugated member. In certain preferred embodiments, the distal portion has at least 1 inch of such hollow, corrugated member, more preferably at least about 3 inches of such material, and most preferably at least about 6 inches of such material. In other embodiments, at least two portions of the central column have sections with such hollow, corrugated member such that a user can preposition each section for a desired bent configuration, thus permitting the ability to reach an object remote form the user that may be difficult or impossible to reach using traditional gripper devices with straight central columns.

In certain embodiments, the hand-held gripping device employs a handle portion that has a second manually-actuatable trigger, with such second trigger able to adjust the orientation of the distally positioned jaw portion by effecting a change in the shape of the one or more corrugated members along the extent of the central portion. In some embodiments, the trigger that functions to alter the bending of the corrugated member is a rotatable knob, such that many varied angular orientations of the distal end (with the jaws) can be attained via rotation of a knob positioned near or on the hand grip of the device. Electronic means can also be employed for such purpose, as well as for the operation of the jaws between their closed and open positions.

While certain embodiments solely employ at least one section of a corrugated member to achieve desired bendable characteristics, other embodiments of the hand-held gripping device have a portion of said central portion that is in telescoping relationship with an adjacent portion of said central portion. Telescoping shafts may have two or more shaft members so long as each inner member is slightly smaller in cross-sectional area than the next outer member. In such embodiments, a locking member associated with said central portion is used to fix two adjacent members of said central portion in an engaged position, with the locking member operable between a first locking position and a second unlocking position. The locking member may comprise a coupling member, such as rotatable collar that can be manipulated by a user to adjust the griping member's length. In one embodiment, a section of corrugated hollow material is positioned at the distal end of the device, about 3 to 6 inches away from the jaws (and in the direction of the hand grip) and two adjacent members of the central column portion are operatively associated with each other in a slidingly telescoping relationship with a locking member is associated with at least one of said two adjacent members, the locking member comprising a selectively radially expandable mandrel radially expanded into engagement with the adjacent members to permit the length of the central column member to be varied.

In preferred embodiments, a pull member comprises first and second pull rods and a cam body supporting a cam is used, with the pull rods associated with the cam support body. The cam is characterized by a first, engaged condition in which the cam is in contact with the second pull rod to thereby fix the length of the pull member, and a second, disengaged condition in which the cam is out of contact with the second pull rod to thereby permit the length of the pull member to be varied. The user-actuatable trigger comprises a manually operable release trigger provided on the handle portion, which is, operatively connected to the cam via a connecting rod.

One of skill in the art, especially guided by the incorporated references, will appreciate the varied types and features of gripping devices that can be constructed and that further incorporate the hollow corrugated member(s) as described herein in order to attain desired bendable capabilities of a particular user. For example, and without limitation, the present invention can be employed in a variety of fields where the problem of access around otherwise difficult angular orientations is presented, such fields including but not limited to the following: fruit pickers; janitors replacing light bulbs, elderly persons grasp objects near their chair, tree pruners; surgeons and dentists/orthodontists to reach interior portions of a person's anatomy, etc.

While preferably the bendable portion of the central column is made of a corrugated material (due to its ability to remain open in its central internal core, thus permitting pull cords to operate therein), those of skill in the art will appreciate that—especially dependent upon how severe and desired bending may be—that other types of bendable segments can be employed to achieve such a function. For example, pliable plastic or rubber-type sections can also be alternatively or in conjunction employed on a gripper device of the present invention so as to achieve the ability of a user to reach objects that would be difficult or nearly impossible using a device having a straight and non-bendable column. Of course, the ability of such a section to uphold the weight of the jaws, especially after the jaws have grasped some desired object, is an important consideration when selecting appropriate materials to employ for the bendable portion of the column. In other words, a sufficient amount of rigidity and/or operational integrity of the central column is required for most applications.

In still other embodiments of the present invention, one or more springs can be employed (with such spring(s) having desired structural integrity with respect to an ability to bend, an ability to support weight that may be encountered when the jaws engage an object and the device is lifted in the air, etc). Thus, in one embodiment, a section of spring is used along the central portion of the device with a cord mechanism that is attached to the jaw end of the device, such that when the cord is pulled, the spring section bends to angularly adjust the jaws such that they can reach around corners otherwise inaccessible with a straight column gripper device.

To comply with appropriate written description and enablement requirements and to provide sufficient guidance in how one of skill in the art can make and use the various and numerous embodiments of the present invention, incorporated herein in their entireties are the following: Hsu, U.S. Pat. Nos. 6,513,844; 6,520,556, 6,739,637, and 4,669,769 to Polder, Jr; 4,962,957 to Traber; 8,061,751 to Hatcher; 7,934,756 to Kroeze; 8,061,751 to Hatcher; 7,665,782 to Buzby et al.; 8,091,936 to Graziano; 7,980,609 to Khubani; 5,895,082 to Kaluzny; 5,590,923 to Berger et al.; as well as U.S. Pat. No. 4,962,957; U.S. Pat. No. 4,709,839; U.S. Pat. No. 3,527,492; U.S. Pat. No. 4,613,179; U.S. Pat. No. 4,669,769; U.S. Pat. No. 6,257,634; U.S. Pat. No. 7,004,520; U.S. Pat. No. 6,513,844; U.S. Pat. No. 6,571,479; and U.S. Pat. No. 6,848,731.

Some extendable tools have fixed tool heads, e.g. a dust mop, or a flexible tool head, e.g. a device for swapping out light bulbs that has spring-like fingers. Other extendable tools include a hand powered actuatable tool head assembly having movable elements, such as, but not limited to, a tree pruner. In other embodiments, extendable tools have an actuatable tool head assembly that have drive assemblies in order to allow the user at the bottom end of the extendable tool to actuate the tool head at the upper end of the extendable tool. While an actuatable tool head assembly associated with one end of an extended tool may be any type of tool, and while the present discussion relates in particular to a tool having a jaw assembly as an example, more specifically a reaching tool that may be used to grip objects between the two jaws, it will be understood by those of skill in the art that various known tool head assemblies can supplant the discussion of clasping jaws and thus, will otherwise suffice to describe the novel and non-obvious aspects of the present invention in such other embodiments and functions.

Thus, as opposed to the prior art, where materials employed for the central column were hardened plastic polymers or any of substantially non-malleable metals, the present invention can be seen as distinctly different as it relates to employing materials and constructions that bend or otherwise flexible so as to achieve the functional attributes that the prior art devices cannot achieve.

BRIEF DESCRIPTION OF THE DRAWINGS

Other advantages of the present invention will be readily appreciated as the same becomes better understood by reference to the following detailed description when considered with the accompanying drawings, wherein:

FIG. 1 is a lateral perspective view of an extendible gripping device according to the present invention;

FIG. 2 is another view of one embodiment showing the corrugated section(s) of the central column near the jaw portion of the inventive gripping device and toward the handle portion of the device.

WRITTEN DESCRIPTION OF A CERTAIN PREFERRED EMBODIMENT

Figure 3:
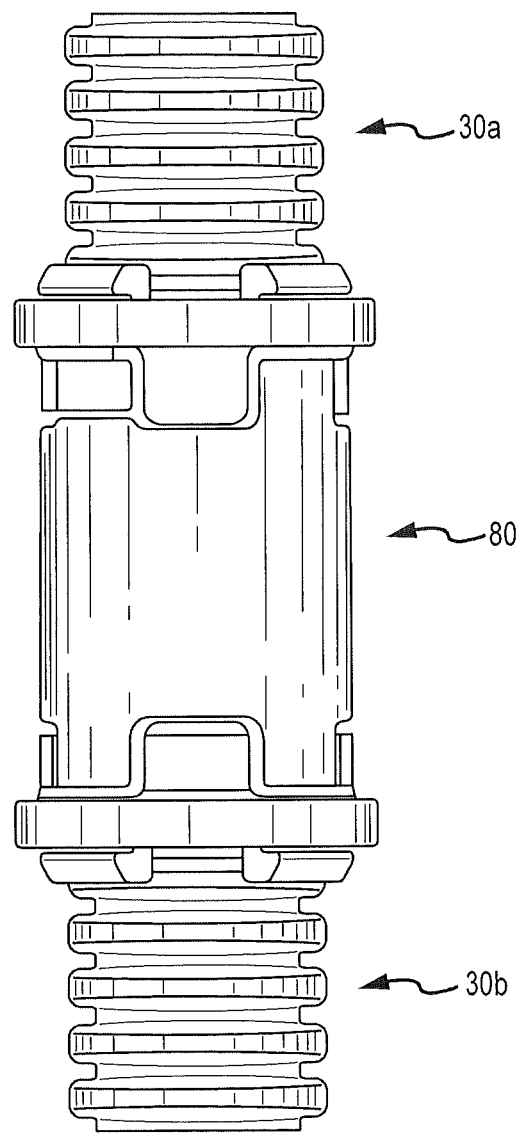
FIG. 3 comprises a perspective close-up view of one embodiment of a corrugated section of the column, showing a dissociable coupling.
Figure 4:
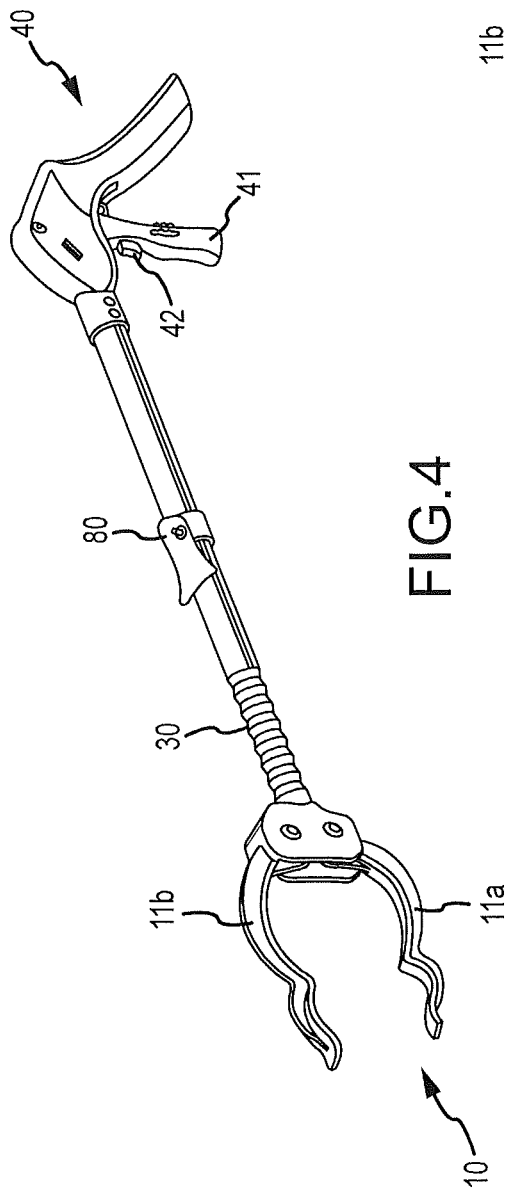
FIG. 4 is a perspective view showing another embodiment with a corrugated segment in addition to a telescoping locking member along the central column.

It will be understood that the disclosed embodiments are merely exemplary of the invention that may be embodied in various and alternative forms. The figures are not necessarily to scale, some features may be exaggerated or minimized to show details of particular components. Therefore, specific structural and functional details disclosed herein are not to be interpreted as limiting, but merely as a representative basis for teaching one skilled in the art to variously employ the present invention. For the following description, the actuatable tool head assembly is described as a gripper having a jaw assembly). It is understood, however, that any type of actuatable tool head assembly may be used.

As disclosed in the figures, various embodiments of the present invention generally comprise a hand-held gripping device having a jaw portion (indicated generally at 10) comprising a pair of jaws 11a, 11b and a handle portion (indicated generally at 40) spaced apart by a selectively extendible central portion (indicated generally at 70). The handle portion 40 comprises a manually-actuatable trigger 41 operatively connected to the jaws of the jaw portion by a pull member. Actuation of the trigger 41 is operative to move the pull member to thereby selectively position the pair of jaws 11a, 11b between fully clamped and fully opened positions thereof. It will be understood that the jaw construction and the handle portion construction is intended as exemplary only, and that those of skill in the art will appreciate how to adapt such portions as desired, consistent only with facilitating operation of the bendable column gripping device as hereinafter described.

A pull member is interconnected with the jaw and handle portions such that manual actuation of the trigger 41 effects movement of the jaws 11a, 11b.

In certain embodiments, the user-actuatable release trigger of the present invention comprises a release button 42 disposed on the trigger 41 of the handle portion 40. In the event that the distance between the jaw portion and the handle portion is not appropriate in light of the task contemplated by the user, the user may adjust the length of the central portion by first unscrewing a collet assembly to thus permit telescoping movement of first and second tubular members. The user next actuates the release trigger, either by depressing the release button or turning the collar (depending on the form of the invention), which actions cause the second coupling to move from the engaged to the disengaged position. At this point, the pull member may be lengthened or shortened concurrently with telescoping movement of the first and second tubular members. Thus, while depressing the release trigger, the user grasps the second tubular member and changes the distance between the handle portion and the gripping portion as desired. After the desired length is obtained, the user releases release trigger and tightens the collet assembly to thereby fix the lengths of each of the central portion and the pull member.

Selective positioning of the first and second tubular members may be effected by rotational movement of one of the first or second tubular members of the central portion.

In certain embodiments, the gripping device of this embodiment comprises a selectively extendible central portion 70 including a first tubular member 71 slidingly telescopingly received within a second, larger-diameter tubular member 73. In order to fix the relative positions of the first 71 and second 73 tubular members, there is provided a collet assembly 80.

A locking mechanism may be provided to fix the pivotal position of the trigger 41, and thereby fix the relative positions of the jaws between the fully open and fully closed positions thereof.

In operation, from the position wherein the jaws are fully opened, a user manually depresses trigger 41 to retract the pull rod 50 and thereby move the jaws toward each other.

To understand and appreciate the varied and numerous applications of the present invention in the context of tools that do not employ the gripping jaw device used as an illustrative example herein, the inventors incorporate by reference herein, in their entireties, the following patents to provide the detailed embodiments that, with the features here described, facilitate far easier access to previously difficult to reach areas so that the various functional assemblies at the remote end of a tool can be used effectively: Hsu, U.S. Pat. Nos. 6,513,844, 6,520,556, and 6,739,637, 4,669,769 to Polder, Jr; 4,962,957 to Traber; 8,061,751 to Hatcher; 7,934,756 to Kroeze; 8,061,751 to Hatcher; 7,665,782 to Buzby et al.; 8,091,936 to Graziano; 7,980,609 to Khubani; 5,895,082 to Kaluzny; 5,590,923 to Berger et al.; as well as U.S. Pat. No. 4,962,957; U.S. Pat. No. 4,709,839; U.S. Pat. No. 3,527,492; U.S. Pat. No. 4,613,179; U.S. Pat. No. 4,669,769; U.S. Pat. No. 6,257,634; U.S. Pat. No. 7,004,520; U.S. Pat. No. 6,513,844; U.S. Pat. No. 6,571,479; and U.S. Pat. No. 6,848,731.

It will be appreciated from the above disclosure that the present invention improves upon the prior art by providing a bendable gripping device that is robust yet simple in design, and that allows easy adjustment of the direction of the jaws to reach around tight corners or other places where a straight columned device would simply not function to retrieve desired objects remote form the user.

In one embodiment, a hand held gripping device is provided that has a jaw portion comprising a pair of jaws that are movable relative to each other between fully clamped and fully open positions. A handle portion is spaced apart from the jaw portion by a selectively extendable portion, the handle portion having a manually actuable trigger connected to the jaw portion. An extendable pole member, preferably running longitudinally through a tubular section, operatively connecting the jaw portion to the handle portion, is provided. Actuation of the trigger is therefore operative to move the pole member to selectively position the pair of jaws between fully clamped and fully opened positions. Between the jaw portion and the handle portion is therefore a central portion, preferably comprising a hollow, corrugated member 30. Such corrugated member 30 preferably has alternating ridges and grooves such that the central portion of the device is able to bend in order to attain predetermined shapes. In particular embodiments, at least one cord is connected between the handle portion and the jaw portion, such that the cord extends through the central portion of the device.

As illustrated in FIG. 2, in certain embodiments of the present invention, two or more corrugated members 30a and 30b are provided at different relative locations along the device, and more specifically along the central portion of the device. In preferred embodiments, at least two thirds of the central portion comprises the corrugated member 30. In still other embodiments, at least a central portion of the device is in a telescoping relationship with an adjacent portion of the device, namely, a first portion 71 is telescopically related to a second portion 73, with a locking member, preferably a locking collar, associated with a central portion. The locking member 80 is provided in a fashion so that the two adjacent members of the central portion 71, 73 may be in an engaged position such that the lengthy of the central portion 70 can be effectively adjusted by the user. The locking member 80 can alternatively be referred to as a coupling member between the two portions 71 and 73. In a preferred embodiment, the locking member comprises a selectively radially expandable mandrel.

In other embodiments, a user actuable trigger comprises two operable triggers with the operation of a first trigger causes the reversal opening and closing of the jaws, whereas the other trigger causes the distal end of the device to move such that the distal end bends in relationship to the longitudinal axis of the device.

In other embodiments, a selective positioning of a knob, such knob position near the trigger/handle portion of the device, is provided in order to cause rotational movement of the distal end of the device through manual adjustment of the knob.

Figure 5:
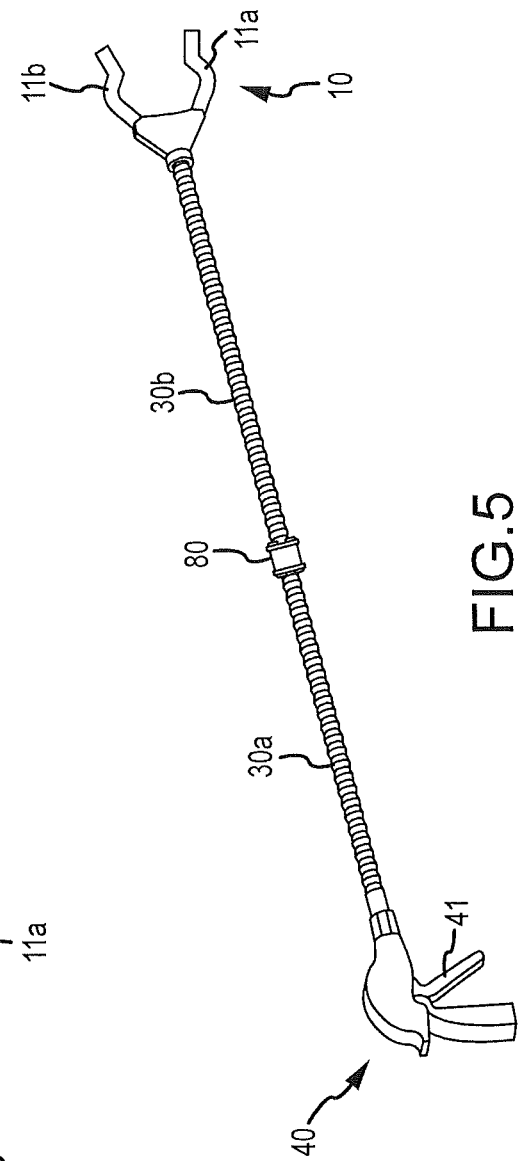
FIG. 5, shows a perspective view of an embodiment where substantially the entire length of the central column comprises a corrugated segment.
Figure 6:
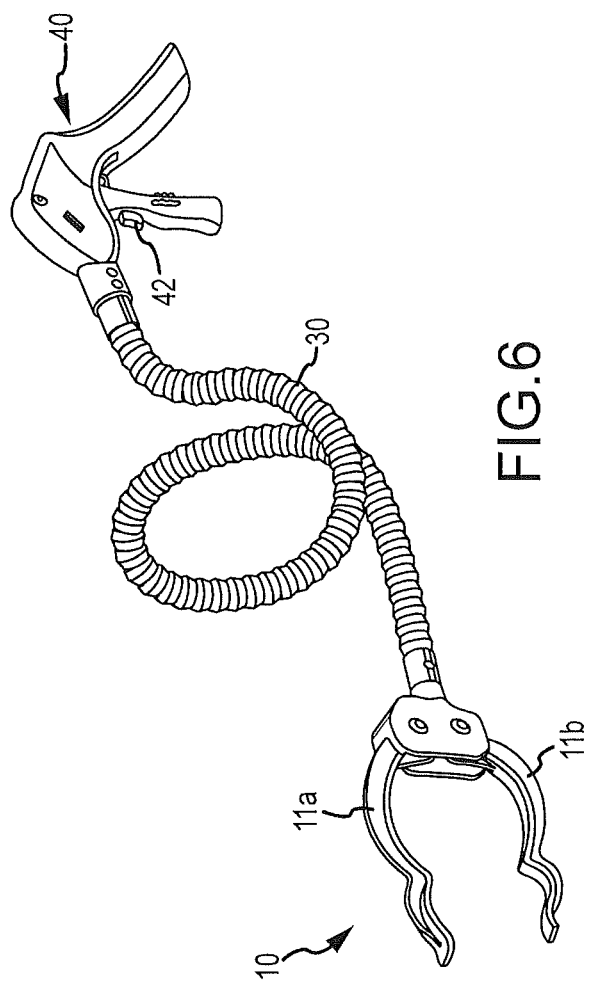
FIG. 6 shows how the corrugated segment can be bent into configurations, including winding the central column around so that the device can be stored and transported easily.

In still other embodiments (for example, FIG. 5) the majority of the portion between the handle portion and the jaw portion comprises corrugated material 30. In such an embodiment, a locking member 80 can be employed, so as to selectively adjust the length of the device in a telescoping relationship, even though the telescoping members themselves are made of a corrugated, bendable material. In other embodiments, however, the locking member 80 can be dispensed with, and the corrugated member 30 can comprise the entirety of the portion between the handle portion and the jaw portion of the device. In such embodiments, it is possible to compress the device in a coiled manner, making transportation and storage of such a device far easier. For example, the bendable nature of the corrugated members used with the device can be employed in order to compact the device to fit within luggage, purses, etc., that may be carried by individuals, especially elderly individuals in need of such a compact, adjustable device.

While embodiments of the invention have been illustrated and described, it is not intended that these embodiments illustrate and describe all possible forms of the invention. Rather, the words used in this specification are words of description rather than limitation, and it is understood that various changes may be made without departing from the spirit and scope of the invention.

What is claimed is:

1. A hand-held gripping device, comprising:
a jaw portion comprising a pair of jaws movable relative to each other between fully clamped and fully opened positions thereof;
a handle portion spaced apart from the jaw portion by a selectively extendible central portion, the handle portion comprising a first manually-actuatable trigger operatively connected to the jaw portion by a selectively extendible pull member at least substantially disposed within the central portion, whereby actuation of the trigger is operative to move the pull member to thereby selectively position the pair of jaws between the fully clamped and fully opened position thereof; said central portion comprising a hollow, corrugated member having alternating ridges and grooves, said corrugated member being bendable so as to attain a predetermined shape; said pull member comprising at least one cord operatively connecting the handle portion to the jaw portion, said at least one cord extending through and entirely encompassed by said central portion; and wherein the corrugated member has a first configuration whereby prior to actuation of the actuation trigger, the pair of jaws is in the fully opened position and the corrugated member is bent;
a locking member operatively associated with said central portion, wherein two adjacent members of the central portion are operatively associated with each other in a slidingly telescoping relationship and said locking member is associated with at least one of said two adjacent members, said locking member comprising a selectively radially expandable mandrel radially expanded into engagement with the at least one of said two adjacent members to permit the length of the pull member to be varied.

2. A hand-held gripping device of claim 1, wherein the central portion comprises glow in the dark material.

3. A hand-held gripping device, comprising:
a jaw portion comprising a pair of jaws movable relative to each other between fully clamped and fully opened positions thereof;
a handle portion spaced apart from the jaw portion by a selectively extendible central portion, the handle portion comprising a first manually-actuatable trigger operatively connected to the jaw portion by a selectively extendible pull member at least substantially disposed within the central portion, whereby actuation of the trigger is operative to move the pull member to thereby selectively position the pair of jaws between the fully clamped and fully opened position thereof, whereby said fully clamped position is achieved when said trigger is pulled;
wherein said central portion comprises a hollow, corrugated member having alternating ridges and grooves, said corrugated member being bendable so as to attain a predetermined shape, said corrugated member constructed of plastic and being bendable so as to attain a predetermined shape; said pull member comprising at least one cord operatively connecting the handle portion to the jaw portion, said at least one cord extending through said corrugated member and being entirely encompassed by said central portion;
wherein the central portion comprises glow in the dark material.

4. A hand-held gripping device, comprising:
a jaw portion comprising a pair of jaws movable relative to each other between fully clamped and fully opened positions thereof;
a handle portion spaced apart from the jaw portion by a selectively extendible central portion, the handle portion comprising a first manually-actuatable trigger operatively connected to the jaw portion by a selectively extendible pull member at least substantially disposed within the central portion, whereby actuation of the trigger is operative to move the pull member to thereby selectively position the pair of jaws between the fully clamped and fully opened position thereof, whereby said fully clamped position is achieved when said trigger is pulled;

wherein said central portion comprises a hollow, corrugated member having alternating ridges and grooves, said corrugated member being bendable so as to attain a predetermined shape, said corrugated member constructed of plastic and being bendable so as to attain a predetermined shape; said pull member comprising at least one cord operatively connecting the handle portion to the jaw portion, said at least one cord extending through said corrugated member and being entirely encompassed by said central portion;

wherein at least two portions of the central portion column comprise said hollow, corrugated member, wherein a user can preposition each of said portions for a desired bent configuration.

5. A hand-held gripping device of claim 4, wherein the central portion comprises glow in the dark material.

6. The device as set forth in claim 4, wherein the central portion comprises at least 6 inches of the hollow, corrugated member.

7. The hand-held gripping device of claim 4, wherein at least a portion of said central portion is in telescoping relationship with an adjacent portion of said central portion.

8. A hand-held gripping device, comprising:
a jaw portion comprising a pair of jaws movable relative to each other between fully clamped and fully opened positions thereof;
a handle portion spaced apart from the jaw portion by a selectively extendible central portion, the handle portion comprising a first manually-actuatable trigger operatively connected to the jaw portion by a selectively extendible pull member at least substantially disposed within the central portion, whereby actuation of the trigger is operative to move the pull member to thereby selectively position the pair of jaws between the fully clamped and fully opened position thereof whereby said fully clamped position is achieved when said trigger is pulled;
wherein said central portion comprises a hollow, corrugated member having alternating ridges and grooves, said corrugated member being bendable so as to attain a predetermined shape, said corrugated member constructed of plastic and being bendable so as to attain a predetermined shape;
said pull member comprising at least one cord operatively connecting the handle portion to the jaw portion, said at least one cord extending through said corrugated member and being entirely encompassed by said central portion; and
wherein the central portion comprises a bendable portion made of two or more corrugated members provided at different relative locations along the central portion of the device.

9. The device as set forth in claim 8, wherein at least two thirds of the central portion comprises the bendable portion.

10. The hand-held gripping device of claim 8, wherein at least a portion of said central portion is in telescoping relationship with an adjacent portion of said central portion.

11. The hand-held gripping device of claim 8, further comprising a locking member associated with said central portion to fix two adjacent members of said central portion in an engaged position, said locking member operable between a first locking position and a second unlocking position.

12. A hand-held gripping device of claim 8, wherein the central portion comprises glow in the dark material.

13. A hand-held gripping device, comprising:
a jaw portion comprising a pair of jaws movable relative to each other between fully clamped and fully opened positions thereof;
a handle portion spaced apart from the jaw portion by a selectively extendible central portion, the handle portion comprising a first manually-actuatable trigger operatively connected to the jaw portion by a selectively extendible pull member at least substantially disposed within the central portion, whereby actuation of the trigger is operative to move the pull member to thereby selectively position the pair of jaws between the fully clamped and fully opened position thereof;
wherein the central portion comprises at least two separate portions comprising a hollow, corrugated member having alternating ridges and grooves, said corrugated member being bendable so as to attain a predetermined shape so that a user can preposition each of said separate portions into a desired bent configuration; and
said pull member comprising at least one cord operatively connecting the handle portion to the jaw portion, said at least one cord extending through said central portion.

14. The hand-held gripping device of claim 13, wherein at least $2/3^{rd}$ of said central portion comprises said corrugated member.

15. The hand-held gripping device of claim 13, wherein at least a portion of said central portion is in telescoping relationship with an adjacent portion of said central portion.

16. The hand-held gripping device of claim 13, further comprising a locking member associated with said central portion to fix two adjacent members of said central portion in an engaged position, said locking member operable between a first locking position and a second unlocking position.

17. The hand-held gripping device of claim 13, further comprising a locking member operatively associated with said central portion.

18. The hand-held gripping device of claim 13, wherein the actuatable trigger comprises a manually operable release trigger.

19. The device as set forth in claim 13, wherein distal portion of the device comprises the hollow, corrugated member.

20. The device as set forth in claim 13, wherein the central portion comprises at least 6 inches of the hollow, corrugated member.

21. The device as set forth in claim 13, wherein the central portion comprises a bendable portion that is adapted to be coiled to facilitate transportation and storage.

22. The device as set forth in claim 13, wherein the central portion comprises at least 3 inches of the hollow, corrugated member.

23. The device as set forth in claim 13, wherein the central portion further comprises a bendable portion made of rubber.

24. The device as set forth in claim 13, wherein the corrugated member is adapted to remain in a coiled configuration to facilitate transportation and storage.

25. A hand-held gripping device of claim 13, wherein the central portion comprises glow in the dark material.

* * * * *